(12) United States Patent
Yang et al.

(10) Patent No.: US 11,631,489 B2
(45) Date of Patent: Apr. 18, 2023

(54) CRANIAL CT-BASED GRADING METHOD AND SYSTEM

(71) Applicant: Union Strong (Beijing) Technology Co. Ltd., Beijing (CN)

(72) Inventors: Guangming Yang, Beijing (CN); Hailan Jin, Beijing (CN); Ling Song, Beijing (CN); Yin Yin, Boston, MA (US); Yangyang Yao, Beijing (CN); Lan Qin, Beijing (CN)

(73) Assignee: UNION STRONG (BEIJING) TECHNOLOGY CO. LTD., Beijing (CN)

( * ) Notice: Subject to any disclaimer, the term of this patent is extended or adjusted under 35 U.S.C. 154(b) by 0 days.

(21) Appl. No.: 15/734,514

(22) PCT Filed: Nov. 14, 2019

(86) PCT No.: PCT/CN2019/118593
§ 371 (c)(1),
(2) Date: Dec. 2, 2020

(87) PCT Pub. No.: WO2020/119376
PCT Pub. Date: Jun. 18, 2020

(65) Prior Publication Data
US 2021/0312624 A1 Oct. 7, 2021

(30) Foreign Application Priority Data

Dec. 14, 2018 (CN) .......................... 201811530861.5

(51) Int. Cl.
*G06K 9/00* (2022.01)
*G16H 30/40* (2018.01)
(Continued)

(52) U.S. Cl.
CPC ........... *G16H 30/40* (2018.01); *G06T 7/0014* (2013.01); *G06V 10/25* (2022.01); *G06V 10/751* (2022.01);
(Continued)

(58) Field of Classification Search
CPC ........ G16H 50/30; G16H 50/20; G16H 30/40; G16H 15/00; A61B 6/5217; A61B 6/504;
(Continued)

(56) References Cited

U.S. PATENT DOCUMENTS 9,159,127 B2 10/2015 Meetz et al.
2010/0183211 A1 7/2010 Meetz et al.
(Continued)

FOREIGN PATENT DOCUMENTS

CN 1270005 A 10/2000
CN 101689301 A 3/2010
(Continued)

OTHER PUBLICATIONS

Yao Shieh and Chien Hung Chang, "Automated ASPECTS Scoring System as a Clinical Support System for Acute Stroke Care", Proceedings of the IEEE-EMBS International Conference on Biomedical and Health Informatics (BHI 2012) Hong Kong and Shenzhen, China, Jan. 2-7, 2012, pp. 691-694 (Year: 2012).*
(Continued)

*Primary Examiner* — Atiba O Fitzpatrick
(74) *Attorney, Agent, or Firm* — Morrison & Foerster LLP

(57) ABSTRACT

Disclosed are a cranial CT-based grading method and a corresponding system, which relate to the field of medical imaging. The cranial CT-based grading method as disclosed solves the problems of relatively great subjective disparities and poor operability in eye-balling ASPECTS assessment. The grading method includes: extracting target areas from
(Continued)

to-be-processed multi-frame cranial CT data; performing infarct judgment on each target area included in the target areas to output an infarct judgment outcome regarding the target area; and outputting a grading outcome based on infarct judgment outcomes regarding all target areas. The grading method and system as disclosed may eliminate or mitigate the diagnosis disparities caused by human factors and imaging deviations due to different imaging equipment, and shorten the time taken by human observation, consideration, and bared-eye grading, thereby serving as a computer-aided method to provide reference for medical studies on stroke.

10 Claims, 4 Drawing Sheets

(51) Int. Cl.
    *G16H 50/30* (2018.01)
    *G16H 50/20* (2018.01)
    *G06T 7/00* (2017.01)
    *G06V 10/25* (2022.01)
    *G06V 10/75* (2022.01)

(52) U.S. Cl.
    CPC ............. *G16H 50/20* (2018.01); *G16H 50/30* (2018.01); *G06T 2207/10081* (2013.01); *G06T 2207/20081* (2013.01); *G06T 2207/20084* (2013.01); *G06T 2207/30016* (2013.01)

(58) Field of Classification Search
    CPC ........... A61B 6/032; A61B 6/507; A61B 6/03; A61B 5/02007; A61B 6/501; A61B 2576/026; A61B 5/0042; A61B 6/5211–5252; G06T 2207/10081; G06T 2207/10072; G06T 2207/30104; G06T 2207/30016; G06T 7/0012–0016; G06T 2207/30004–30104; G06T 2207/20021; G06T 7/11; G06T 2207/30096; G06T 7/0014; G06T 2207/20081; G06T 2207/20084; G06V 2201/03; G06V 10/751

See application file for complete search history.

(56) References Cited

U.S. PATENT DOCUMENTS

| 2012/0114205 | A1 | 5/2012 | Tang | |
|---|---|---|---|---|
| 2016/0157800 | A1* | 6/2016 | Goyal | A61B 6/486 |
| | | | | 600/431 |
| 2019/0274652 | A1* | 9/2019 | Goyal | G16H 30/40 |
| 2021/0098115 | A1* | 4/2021 | Shin | G06T 5/002 |
| 2022/0020152 | A1* | 1/2022 | Orasanu | G06T 7/0014 |

FOREIGN PATENT DOCUMENTS

| CN | 105997128 A | 10/2016 |
|---|---|---|
| CN | 109671069 A | 4/2019 |
| CN | 109685123 A | 4/2019 |
| CN | 109712122 A | 5/2019 |
| EP | 2158575 A2 | 3/2010 |
| JP | 2010530270 A | 9/2010 |
| WO | 2008155718 A2 | 12/2008 |

OTHER PUBLICATIONS

Su-min Jung, Taeg-keun Whangbo, "Evaluating a Deep-Learning System for Automatically Calculating the Stroke ASPECT Score", International Conference on Information and Communication Technology Convergence (ICTC), Conference Date: Oct. 17-19, 2018, Date on IEEE Xplore: Nov. 19, 2018, pp. 564-567 (Year: 2018).*
Iris Quasar Grunwald, Andreas Ragoschke-Schumm, Michael Kettner, et al. "First Automated Stroke Imaging Evaluation via Electronic Alberta Stroke Program Early CT Score in a Mobile Stroke Unit", Cerebrovasc Diseases 2016;42:pp. 332-338, DOI: 10.1159/000446861 (Year: 2016).*
Diogo C. Haussen, Seena Dehkharghani, Srikant Rangaraju, "Automated CT Perfusion Ischemic Core Volume and Noncontrast CT ASPECTS (Alberta Stroke Program Early CT Score)", Stroke, 2016—Am Heart Assoc, Aug. 9, 2016, 2016;47:2318-2322 (Year: 2016).*
Puetz, V. et al. (Sep. 1, 2008). "Extent of Hypoattenuation on CT Angiography Source Images Predicts Functional Outcome In Patients With Basilar Artery Occlusion," Stroke 39(9):2485-2490.
Chawla, M. et al. (Sep. 2009). "A method for automatic detection and classification of stroke from brain CT images," in 2009 Annual International Conference of The IEEE Engineering In Medicine And Biology Society, 3581-3584, 6 pages.
Hampton-Till, J. et al. (Aug. 2015). "Automated Quantification of Stroke Damage on Brain Computed Tomography Scans: e-ASPECTS," EMJ Nerol. 3(1):69-74, 7 pages.
International Search Report dated Feb. 1, 2020, for International Patent Application No. PCT/CN2019/118593, filed Nov. 14, 2019, 3 pages.
Wang, K.-Y. et al. (May 2012) "A New Anomaly Detection Algorithm for Brain CT Image," Computer Technology and Development 22(5):185-187 (English Abstract).

* cited by examiner

| Area\Greyscale | Left | Right | Ratio | Difference |
|---|---|---|---|---|
| M1 | 31.8 | 32.3 | 0.99/1.02 | -0.5/0.5 |
| M2 | 30.1 | 32.8 | 0.92/1.09 | -2.7/2.7 |
| M3 | 30.2 | 32.6 | 0.93/1.08 | -2.4/2.4 |
| C | 36.1 | 36.1 | 1.0/1.0 | 0/0 |
| I | 33.5 | 33.3 | 1.01/0.99 | 0.2/-0.2 |
| IC | 33.3 | 32.4 | 1.03/0.97 | 0.9/-0.9 |
| L | 37.0 | 37.5 | 0.99/1.01 | -0.5/0.5 |
| M4 | 32.0 | 30.4 | 1.05/0.95 | 1.6/-1.6 |
| M5 | 31.0 | 31.0 | 1.0/1.0 | 0/0 |
| M6 | 32.6 | 32.6 | 1.0/1.0 | 0/0 |

CRANIAL CT-BASED GRADING METHOD AND SYSTEM

CROSS REFERENCE TO RELATED APPLICATIONS

This application is a national stage application under 35 U.S.C. § 371 of International Application No. PCT/CN2019/118593, filed internationally on Nov. 14, 2019 which claims the benefit of Chinese Application No. 201811530861.5, filed Dec. 14, 2018, the contents of which are incorporated herein by reference in their entirety.

FIELD

The present disclosure relates to the field of medical imaging and computer technologies, and more particularly relates to a cranial CT-based grading method and a corresponding system.

BACKGROUND

ASPECTS (Alberta Stroke Program Early CT Score), proposed by Barber et al. in 2000, offers a significant reference for stroke diagnosis and treatment. According to the ASPECTS grading method, the middle-cerebral-artery (MCA) territory of an acute stroke patient is divided into 10 areas of interest based on his or her cranial CT data, including: C-Caudate head; L—lentiform nucleus, IC—internal capsule Post Limb, I— insular ribbon, M1—anterior MCA cortex, M2—MCA cortex lateral to insular ribbon, M3—posterior MCA cortex, which are located at the ganglionic level, and M4—anterior MCA territory immediately superior to M1, M5—lateral MCA territory immediately superior to M2, and M6—posterior MCA territory immediately superior to M3, which are located at the supraganglionic level. The above 10 areas are allotted the same weight, i.e., 1 point for each area, such that the total ASPECTS value is 10 points. A value resulting from subtracting the number of areas with early ischemic changes from the total score serves as the grading outcome, offering a reference for disease diagnosis and treatment. The above grading method mainly addresses anterior circulation. With further in-depth studies on stroke, Puetz et al. proposed PC-ASPECTS (Posterior Circulation Acute Stroke Prognosis Early CT Score) in 2008. The PC-ASPECTS grading method mainly scores the bilateral thalami, the bilateral cerebella, the bilateral posterior cerebral artery (PCA) territories, the midbrain, and the pons, wherein a 1-point weight is allotted to each of the bilateral thalami, bilateral cerebella, bilateral posterior cerebral artery (PCA) territories, and a 2-point weight is allotted to each of the midbrain and pons; as such, the total PC-ASPECTS value is 10 points. A value resulting from subtracting the weighted points corresponding to the areas with early ischemic changes from the total score serves as the grading outcome, offering a reference for disease diagnosis and treatment.

In current clinical applications, irrespective of the anterior-circulation ASPECTS measurement or the posterior-circulation ASPECTS measurement, they mainly rely on eye-balling assessment. However, due to factors such as different imaging equipment, different clinicians, and different patient conditions, the agreement between interpretations of the cranial CT data cannot be guaranteed, such that eye-balling assessment of ASPECTS will lead to a great subjective disparity. Therefore, such "eye-balling assessment" approach has a poor operability. On the other hand, the stroke condition develops very rapidly, and blood supply interruption of over 4 or 5 minutes would cause permanent and irreversible infarct, resulting in a very high dependence/death rate; further, the boundaries of tissue partitions on the CT are difficult to discern, such that if the partitions cannot be determined quickly and accurately, diagnosis and treatment will be delayed.

Therefore, a grading method is currently desired, which may eliminate or mitigate diagnosis disparities caused by human factors including technical level, operating technique, imaging quality, human eye discernibility, fatigue degree, and different cognitive experience, as well as the diagnosis disparities caused by imaging deviations between different imaging equipment, and shorten the time taken by human observation, consideration, and eye-balling grading, so as to serve as a computer-aided method to provide objective references for medical studies on stroke.

SUMMARY

Embodiments of the present disclosure provide a cranial CT-based grading method and a corresponding system so as to eliminate or mitigate diagnosis disparities due to subjective factors and objective factors such as imaging deviations between different image equipment, shorten the time taken by grading, and enhance diagnosis efficiency and accuracy.

An embodiment of the present disclosure provides a cranial CT-based grading method, comprising steps of:

extracting target areas from to-be-processed multi-frame cranial CT data, wherein the target areas refer to areas for being graded in the cranial CT data;

performing infarct judgment on each target area included in the target areas to output an infarct judgment outcome regarding the target area; and outputting a grading outcome based on infarct judgment outcomes regarding all target areas.

Preferably, the extracting target areas from to-be-processed multi-frame cranial CT data specifically comprises:

inputting the to-be-processed cranial CT data into a model, and classifying each pixel point in the cranial CT data using digital labels to output a three-dimensional matrix with digital labels, the three-dimensional matrix being in correspondence with respective pixel points in the cranial CT data, wherein the digital labels are in one-to-one correspondence with the target areas.

Preferably, the performing infarct judgment on each target area included in the target areas to output an infarct judgment outcome regarding the target area specifically comprises:

performing infarct judgment on each pixel point included in the target area to output an infarct judgment outcome regarding the target area.

Further, the performing infarct judgment on each target area included in the target areas to output an infarct judgment outcome regarding the target area further comprises:

judging, based on the infarct judgment outcome regarding the target area, whether infarct is indicated in the target area in both left and right cerebral hemispheres; and if infarct is indicated in the target area in both left and right cerebral hemispheres, further determining which specific side is infarcted, and correcting the infarct judgment outcome regarding the target area as an updated infarct judgment outcome regarding the target area.

Preferably, the outputting a grading outcome based on infarct judgment outcomes regarding all target areas specifically comprises:

determining all infarcted target areas based on the infarct judgment outcomes regarding all target areas; and;

subtracting, based on weights allotted to respective target areas, weights of the infarcted target areas from the total score to output a resulting value as the grading outcome.

An embodiment of the present disclosure provides a cranial CT-based grading system, comprising:

an area extracting module configured for extracting target areas from to-be-processed multi-frame cranial CT data, wherein the target areas refer to areas for being graded in the cranial CT data;

an infarct identifying module configured for performing infarct judgment on each target area included in the target areas to output an infarct judgment outcome regarding the target area; and a grading module configured for outputting a grading outcome based on infarct judgment outcomes regarding all target areas.

Preferably, the extracting target areas from to-be-processed multi-frame cranial CT data specifically comprises:

inputting the to-be-processed multi-frame cranial CT data into a model, and classifying each pixel point in the cranial CT data using digital labels to output a three-dimensional matrix with digital labels, the three-dimensional matrix being in correspondence with respective pixel points in the cranial CT data, wherein the digital labels are in one-to-one correspondence with the target areas.

Preferably, the performing infarct judgment on each target area included in the target areas to output an infarct judgment outcome regarding the target area specifically comprises:

performing infarct judgment on each pixel point included in the target area to output an infarct judgment outcome regarding the target area.

Further, the performing infarct judgment on each target area included in the target areas to output an infarct judgment outcome regarding the target area further comprises:

judging, based on the infarct judgment outcome regarding the target area, whether infarct is indicated in the target area in both left and right cerebral hemispheres; and if infarct is indicated in the target area in both left and right cerebral hemispheres, further determining which specific side is infarcted, and correcting the infarct judgment outcome regarding the target area as an updated infarct judgment outcome regarding the target area.

Preferably, the outputting a grading outcome based on infarct judgment outcomes regarding all target areas specifically comprises:

determining all infarcted target areas based on the infarct judgment outcomes regarding all target areas; and;

subtracting, based on weights allotted to respective target areas, weights of the infarcted target areas from the total score to output a resulting value as the grading outcome.

At least one of the technical solutions above adopted in the embodiments of the present disclosure may achieve the following beneficial effects:

By means of extracting target areas from to-be-processed multi-frame cranial CT data to perform infarct judgment on the respective target areas and then outputting a grading outcome, the embodiments of the present disclosure may eliminate or mitigate the diagnosis disparities caused by human factors as well as the diagnosis disparities caused by imaging deviations between different imaging equipment, and shorten the time taken by human observation, consideration, and eye-balling grading, so as to serve as a computer-aided method to enhance diagnosis efficiency and accuracy.

BRIEF DESCRIPTION OF THE DRAWINGS

To elucidate the technical solutions of the present disclosure or the technical solutions in the prior art, the drawings used in describing the embodiments of the present disclosure or the prior art will be briefly introduced below. It is understood that the drawings as described only relate to some embodiments of the present disclosure. To those skilled in the art, other drawings may be derived based on these drawings without exercise of inventive work, wherein.

NOTES

Figure 3A:
FIG. 3a is a schematic diagram of pons and bilateral cerebellar areas subjected to PC-ASPECTS grading according to an embodiment of the present disclosure.
Figure 3B:
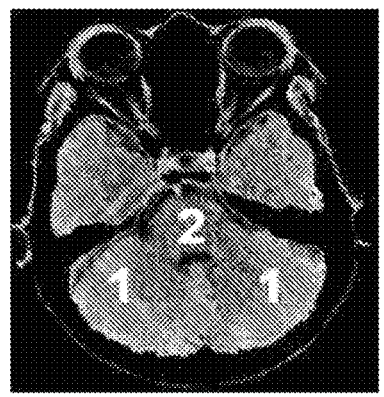
FIG. 3b is a schematic diagram of the midbrain area subjected to PC-ASPECTS grading according to an embodiment of the present disclosure.
Figure 3C:
FIG. 3c is a schematic diagram of the bilateral thalami and bilateral PCA-territories subjected to PC-ASPECTS grading according to an embodiment of the present disclosure.

In FIG. 3a, pons and bilateral cerebella from top to down;
In FIG. 3c, bilateral thalami and bilateral PCA-territories from top to down;
In FIG. 3, the numbers 1 and 2 represent the weights of respective areas.

DETAILED DESCRIPTION OF EMBODIMENTS

To facilitate those skilled in the art to understand, the technical solutions of the present disclosure will be described in a clear and comprehensive manner with reference to the accompanying drawings; it is apparent that the embodiments described herein are only part of the embodiments of the present disclosure, rather all of them. All other embodiments obtained by those skilled in the art without exercise of inventive work based on the embodiments in the present disclosure shall fall within the protection scope of the present disclosure.

Figure 1:
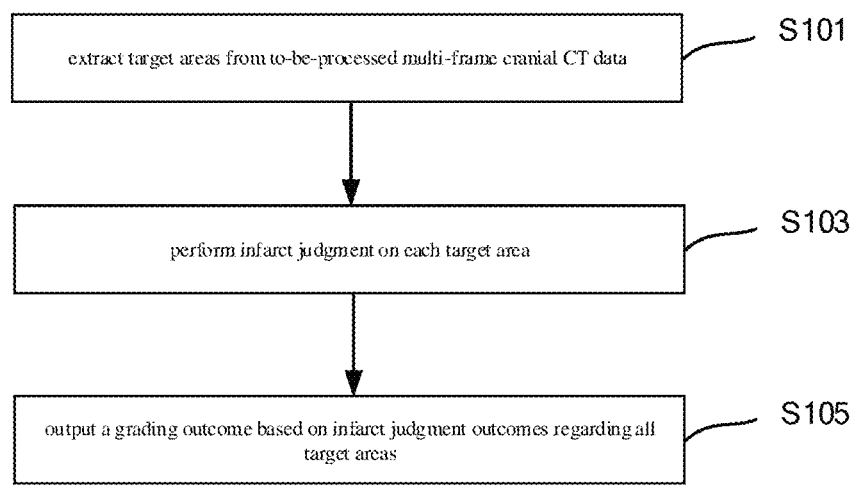
FIG. 1 is an outline diagram of a cranial CT-based grading method according to an embodiment of the present disclosure.

FIG. 1 is a frame diagram of a cranial CT-based grading method according to an embodiment of the present disclosure, specifically comprising steps of:

Step S101: extracting target areas from to-be-processed multi-frame cranial CT data.

A CT is made up of a certain number of pixel points with different greyscales from black to white in a matrix arrangement. A CT number is a measurement of intensity of a corresponding human body tissue. As a single frame of CT is a sectional (typically cross-section) image with a certain thickness, a plurality of continuous sectional images are needed to display an entire organ. Therefore, when performing ASPECTS assessment, a series of multi-frame images need to be observed for giving assessment; in this embodiment, the to-be-processed cranial CT data all have multiple frames.

Figure 2A:
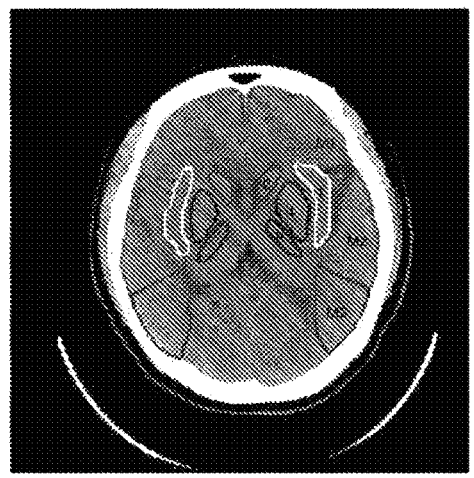
FIG. 2a is a schematic diagram of applying ASPECTS grading to the ganglionic level according to an embodiment of the present disclosure.
Figure 2B:
FIG. 2b is a schematic diagram of applying ASPECTS grading to the supraganglionic level according to an embodiment of the present disclosure.

In an embodiment of the present disclosure, the 10 areas subjected to anterior-circulation ASPECTS assessment are respectively located at the ganglionic level and the supraganglionic level, as specifically shown in FIG. 2. Therefore, when performing anterior-circulation ASPECTS assessment, it is needed to determine the locations of respective 10 areas in the left and right cerebral hemispheres. Specifically, it is needed to determine whether respective pixel points in respective frames of the to-be-processed multi-frame CT data belong to the target areas in the left and right cerebral hemispheres and to which specific areas of the target areas they belong. The target areas refer to areas for being graded in the to-be-analyzed cranial CT; by judging cerebral infarct conditions of the target areas, the cranial CT may be graded. In an embodiment of the present disclosure, the target areas may refer to the caudate heads, lentiform nuclei, internal capsules Post Limb, insular ribbons, and M1-M6 areas in the left and right cerebral hemispheres, wherein there are 20 areas in total. When a pixel point does not belong to any of the target areas, it is determined to belong to the background area. With the trained extraction model, the target areas may be extracted, wherein the cranial CT data are inputted into the extraction model and then a three-dimensional matrix with digital labels is outputted, the digital labels being in one-to-one correspondence with the target areas in the left and right hemispheres.

In another embodiment of the present disclosure, among the 8 areas for posterior-circulation ASPECTS assessment, the pons and bilateral cerebella are located in the cerebellar territory, the midbrain is located in the midbrain territory, and the bilateral thalami and the bilateral PCA-territories are located in the cerebral territory, as specifically shown in FIG. 3. Specifically, when performing posterior-circulation ASPECTS assessment, it is needed to determine whether respective pixel points in respective frames of the to-be-processed multi-frame CT belong to the target areas and to which specific target areas they belong. The target areas refer to areas for being graded in the to-be-analyzed cranial CT. By judging cerebral infarct of the specific target area, the cranial CT may be graded. In an embodiment of the present disclosure, the target areas may refer to the pons, bilateral cerebella, midbrain, bilateral thalami, and bilateral PCA-territories, wherein there are 8 areas in total. When a pixel point does not belong to any of the target areas, it is determined to belong to the background area. With the trained extraction model, the target areas may be extracted, wherein the cranial CT data are inputted into the extraction model and then a three-dimensional matrix with digital labels is outputted, the digital labels being in one-to-one correspondence with the target areas.

Step S103: performing infarct judgment on respective target areas to output infarct judgment outcomes regarding all target areas.

After extracting the target areas in step S101, it is needed to further analyze and judge which areas are infarcted. In a CT, one CT number corresponds to one greyscale. Infarct may be determined in a plurality of manners. An exemplary manner is based on the symmetric property of human brains: the CT numbers of normal human brain tissues at symmetrical positions in the left and right cerebral hemispheres are substantially identical, i.e., their greyscale values are substantially identical. However, if a brain tissue at one side is infarcted, its greyscale value will decline; therefore, by comparing with the greyscales of the corresponding areas in the contralateral hemisphere, the areas of infarct may be determined, thereby implementing infarct judgment on respective target areas included in the target areas.

Besides the approach indicated above, another exemplary manner of infarct judgment is to first extract features, e.g., greyscale information, greyscale information of a neighboring pixel point, gradient information, and gradient information of the neighboring pixel point, etc., and then train a model by supervised learning, which may also implement infarct judgment.

In normal circumstances, when the cerebral infarct occurs, it occurs only to one side; if it occurs to both sides, the cerebral tissues are possibly already dead. Therefore, if the infarct judgment outcome regarding the target area shows presence of early ischemia changes in both left and right cerebral hemispheres, the infarct judgment outcome of a certain side might be caused by noises such as image artifacts. Based on the above reasons, if the infarct judgment outcome show presence of early ischemia changes in both left and right cerebral hemispheres, it is needed to further determine which specific side is infarcted so as to correct the infarct judgment outcome. Upon correction, the judgment may be made based on greyscale variations. For bilateral target areas, the smaller the ratio between bilateral greyscales, or the smaller the difference between bilateral greyscales, or the smaller the numerical value resulting from the combination of the ratio and the difference, the higher the confidence is; therefore, by comparing the minimum values among the ratios between bilateral greyscales, or the minimum differences between bilateral greyscales, or the minimum numerical values resulting from the combinations of the ratios and the differences in the bilateral target areas, the side with the smaller value, i.e., the side with a higher confidence, is determined to be infarcted, while the contralateral hemisphere is determined as not infarcted; the above outputted infarct judgment outcome is then corrected based on the confidence outcome.

Step S105: outputting a grading outcome based on infarct judgment outcomes regarding all target areas.

In normal circumstances, the total scores of the anterior-circulation ASPECTS and the posterior-circulation ASPECTS are both 10 points; when infarct occurs, the ASPECTS value will decline. Based on the determined infarct judgment outcome, the score obtained by subtracting the points of infarcted areas from the 10 points based on the weights allotted to respective target areas is the final score, thereby implementing grading of the cranial CT.

Grading the cranial CT by the method provided in this embodiment may eliminate or mitigate diagnosis disparities caused by human factors as well as the diagnosis disparities caused by imaging deviations between different imaging equipment, which greatly reduces the time taken by human observation and consideration.

Figure 4:
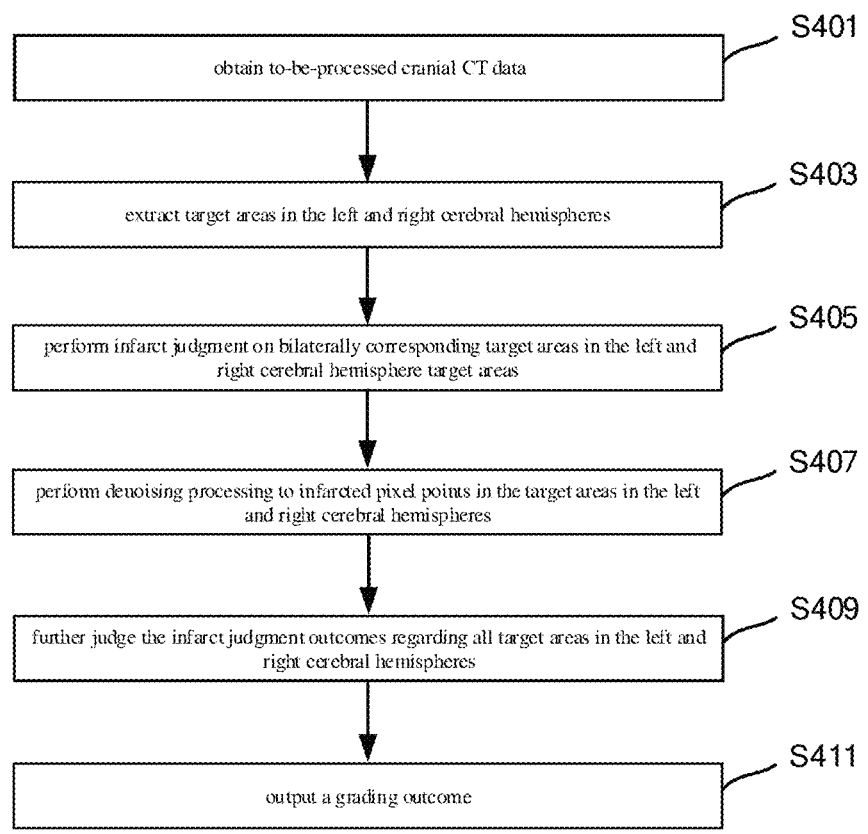
FIG. 4 is a flow diagram of a cranial CT-based grading method according to an embodiment of the present disclosure.

To further illustrate the cranial CT-based grading method, FIG. 4 is a flow diagram of a cranial CT-based grading method according to an embodiment of the present disclosure, wherein the grading process is illustrated in detail with the anterior-circulation ASPECTS as an example.

Step S401: obtaining to-be-processed cranial CT data.

In a CT, different pixel sizes result in correspondingly different numbers of pixels. For example, the pixel size may be 1.0 mm*1.0 mm or 0.5 mm*0.5 mm, and the corresponding number of pixels may be 256*256 or 512*512. Apparently, the smaller the pixel size, the larger the number of pixels, and the higher the spatial resolution. As the CT data is a sectional image, a plurality of continuous sectional images are needed to display an entire organ; therefore, the to-be-processed cranial CT has multiple frames.

Step S403: extracting target areas in the left and right cerebral hemispheres.

To extract the target areas in the left and right hemispheres, it is needed to classify, using digital labels, each pixel point in the to-be-processed multi-frame CT so as to determine to which specific area the pixel point belongs in the target areas in the left and right cerebral hemispheres. In an embodiment of the present disclosure, 0 represents the background, 1, represents the left M1, 2 represents the left M2, 3 represents the left M3, 4 represents the left caudate head, 5 represents the left insular ribbon, 6 represents the left internal capsule Post Limb, 7 represents the left lentiform nucleus, 8 represents the right M1, 9 represents the right M2, 10 represents the right M3, 11 represents the right caudate head, 12 represents the right insular ribbon, 13 represents the right internal capsule Post Limb, 14 represents the right lentiform nucleus, 15 represents the left M4, 16 represents M5, 17 represents the left M6, 18 represents the right M4, 19 represents the right M5, and 20 represents the right M6. The to-be-processed multi-frame CT data are subject to a neural network or other algorithms to output a three-dimensional matrix with a digital label, wherein the values in the matrix are 0~20, among which, 1-20 represent target areas. If the input data are a 30*512*512 image, which represents 30 frames of CT data, the CT data of each frame being 512*512, then a three-dimensional matrix with a digital label 30*512*512 is outputted, wherein the three-dimensional matrix is in correspondence with the cranial CT.

Step S405: performing infarct judgment on bilaterally corresponding target areas in the left and right cerebral hemisphere target areas.

The target areas extracted in step S403 need to be subjected to further infarct judgment. A CT number is a measurement of relative intensity in a CT, a unit of which is Housefield Unit (HU); CT numbers of human tissues have fixed ranges. For example, the CT number of water is 0; the CT number of blood ranges from 60 to 100HU, the CT number of grey matter ranges from 30 to 35HU, the CT number of white matter ranges from 20 to 25 HU, the CT number of muscles ranges from 20 to 40 HU, and the CT number of bones is greater than 1000 HU. In a CT, one CT number corresponds to one greyscale. Due to the symmetrical property of human brains, in normal conditions, the mean CT numbers of human brain tissues at symmetrical positions in the left and right cerebral hemispheres are substantially identical, i.e., their greyscale values are substantially identical. However, if the brain tissues at one side are infarcted, their greyscale value will decline; therefore, by comparing with the greyscale of the corresponding area in the contralateral hemisphere, an infarcted area may be determined.

Based on the digital label outputted in step S403, symmetrical target areas in the left and right cerebral hemispheres in the CT are located; all pixel points in the target areas are traversed; meanwhile, to eliminate interference such as noises, thresholds thre0 and thre1 are set; the pixel points with greyscale values between thre0 and thre1 are selected, wherein thre0 may be set to 30HU and thre1 may be set to 50HU. The greyscale values of all eligible pixel points in one target area are summed and then averaged, wherein the average value serves as the average greyscale value of the target area; by comparison between the greyscale value of the target area at one side with the greyscale value of the contralateral target area, whether the target area is infarcted may be determined.

In an embodiment of the present disclosure, infarct judgment may be made by extracting image features. Specifically, image features, such as greyscale information, greyscale information of a neighboring pixel point, gradient information, and gradient information of the neighboring pixel point, are extracted and manually labelled and then trained by supervised learning such as SVM (Support Vector Machine) and random forest, etc. With the trained model, image features of each pixel point in the image are extracted to obtain the infarct judgment outcome regarding said each pixel point. Specifically, with this approach, the outputted infarct judgment outcomes are dichotomic, i.e., 0 indicates not infarcted, and 1 indicates infarcted.

Figures 5, 6:
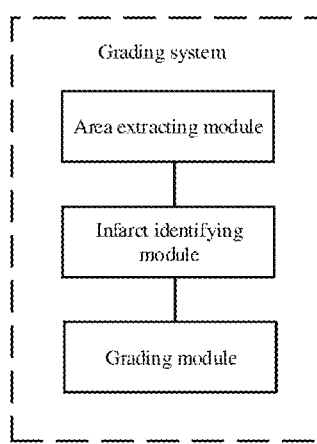
FIG. 5 shows a schematic diagram of determining the frames where the ganglionic level and the supraganglionic level are located according to an embodiment of the present disclosure.
FIG. 6 is a schematic diagram of performing infarct judgment according to an embodiment of the present disclosure.

FIG. 5 is a schematic diagram of infarct judgment according to an embodiment of the present disclosure. Specifically, the judgment may be made by a difference algorithm, a ratio algorithm, and a combination of the ratio algorithm and the difference algorithm; any other algorithms of infarct judgment based on greyscale changes are regarded as equivalents to the algorithms adopted in the present disclosure. For example, to determine whether a lentiform nucleus is infarcted, a point (with the digital label 7) in the left lentiform nucleus and a point (with the digital label 14) in the right lentiform nucleus in the image data are located; all pixel points corresponding to the digital label 7 and the digital label 14 are traversed to respectively screen pixel points with a greyscale value between 30HU and 50HU among the pixel points with the digital label 7 and the digital label 14. With the screened pixel points with the digital label 7 and the digital label 14, the mean value of the greyscale values of the pixel points with the digital label 7 is computed as the greyscale value for the left lentiform nucleus; the mean value of the greyscale values of the pixel points with the digital label 14 is computed as the greyscale value for the right lentiform nucleus; the greyscale value of the left lentiform nucleus and the greyscale value of the right lentiform nucleus are then compared to determine whether there is an infarcted lentiform nucleus and the lentiform nucleus at which side is infarcted. Other algorithms of computing the mean greyscale value, e.g., subjecting the greyscale value of each pixel point to certain operation and conversion, e.g., greyscale stretch, are all regarded as equivalent to the algorithms adopted in the present disclosure.

In an embodiment of the present disclosure, infarct judgment is made using a difference algorithm; it is believed that in corresponding target areas in the left and right cerebral hemispheres, if the difference between the greyscale value of a certain target area at one side and the greyscale value of the contralateral target area is less than a preset threshold cliff, a corresponding area in the cranial CT is believed to be infarcted, wherein the side with the lower greyscale value is the infarcted side. Generally, the threshold diff is −2. For example, in the embodiment shown in FIG. 5, the difference between the greyscale value of the left M2 area and the greyscale value of the right M2 area is −2.7, less than the threshold −2; then, it is believed that the left M2 area is infarcted. With the same algorithm, it is determined that the left M3 and the right M4 are infarcted.

In an embodiment of the present disclosure, infarct judgment is made using a ratio algorithm; it is believed that in corresponding target areas in the left and right cerebral hemispheres, if the ratio value between the greyscale value of a target area at one side and the greyscale value of the contralateral target area is less than a preset threshold ratio, a corresponding area in the cranial CT is infarcted, wherein the side with the lower greyscale value is the infarcted side. Generally, the threshold ratio is 0.96. For example, in the embodiment of FIG. 6, the ratio between the left lentiform nucleus and the right-side lentiform nucleus is 0.99, greater than 0.96; then, it is believed that the lentiform nuclei are not infarcted, in agreement with the judgment outcome of the difference algorithm. The ratio between the greyscale value of the left M2 area and the greyscale value of the right M2 area is 0.92, less than 0.96; then it is believed that the left M2 area is infarcted. With the same algorithm, it is determined that the left M3 is infarcted.

In an embodiment of the present disclosure, infarct judgment is made by an algorithm combining the ratio algorithm and the difference algorithm. It is believed that the basis for infarct is ratio<0.96 and difference<−2. In the embodiment of FIG. 5, this approach is adopted to perform infarct judgment on the target areas in the cranial CT, wherein the left M2, M3 and the right M4 are infarcted. The basis for infarct judgment may also be ratio<0.96 or difference<−2. In the embodiment of FIG. 5, the same approach is adopted to perform infarct judgment, wherein the left M2 and M3 are infarcted.

Generally, the CT number of a tissue with early ischemia change is not lower than 20HU; supposing that the cerebral tissues of a target area at the contralateral hemisphere are not infarcted, which have a mean greyscale value of about 40Hu, then the ratio between the greyscales of the bilateral target areas cannot be less than 0.5 and the absolute value of the difference diff cannot be greater than 20. In an embodiment of the present disclosure, c=(ratio−0.5)/0.7+(diff+20)/50 may be adopted to perform infarct judgment on a target area in the cranial CT; if the value is less than or equal to 1, it is believed that the cerebral tissue in the target area at that side is infarcted; if greater than 1, not infarcted. In the embodiment of FIG. 6, the difference of the right M4 area is −1.6 and the ratio is 0.95; (0.95−0.5)/0.7+(−1.6+20)/50=1.02>1, then it is believed that the M4 area is not infarcted. With this algorithm, the left M2 and M3 areas are determined to be infarcted.

Based on the algorithms of extracting target areas provided in the embodiments of the present disclosure, because each target area has a certain thickness while the slice thickness of a CT is relatively small, each target area included in the extracted target areas is at least present in one frame of the CT. When performing infarct judgment using the above infarct judgment algorithms, each frame of a target area needs to be judged. For a same target area which is present in at least two frames of the CT, it is likely that the target area is infarcted in one or more frames of the CT, but not infarcted in one or more other frames of the CT; as long as a certain target area is infarcted in one frame, it is believed that the target area is infarcted. Specifically, the extracted target areas, e.g., the bilateral lentiform nuclei, are respectively located in the $10^{th}$ frame of CT and the $11^{th}$ frame of CT; based on the infarct judgment outcomes, the left lentiform nucleus in the $10^{th}$ frame of CT is infarcted, while the left lentiform nucleus in the $11^{th}$ frame of CT is not infarcted; in this case, it is believed that the left lentiform nucleus is infarcted.

After infarct judgments are completely done to the to-be-processed multi-frame CT data, the infarct judgment outcomes regarding the 20 target areas are outputted for subsequent grading. The infarct judgment outcomes above are each represented by an array including three elements. The first element of the array is a Boolean data type, wherein 0 represents not infarcted, and 1 represents infarcted; the second element is a floating-point number, which is the result of dividing the mean greyscale value of a certain target area at the present side by the mean greyscale value of the contralateral target area; the third element is a floating-point number, which is the result of the mean greyscale value of the target area at the present side minus the mean greyscale value of the contralateral target area. For example, the first output is [0, 1, 0), wherein 0 indicates that the left M1 area is not infarcted, the mean greyscale value of the left M1 area divided by the mean greyscale value of the right M1 area is 1, and the mean greyscale value of the left M1 territory minus the mean greyscale value of the right M1 area is 0.

Step S407: performing denoising processing to the infarcted pixel points in the target areas in the left and right cerebral hemispheres.

Respective pixel points in the target areas have been classified in step S405. Isolated infarcted pixel points might be existent among the pixel points of these areas. Such isolated infarcted pixel points are possibly caused by factors such as imaging quality and imaging equipment, which belong to interference noises; therefore, it is needed to remove these noises to prevent affecting the subsequent grading.

The infarct judgment outcomes with removal of isolated pixel points need to be corrected. If an infarct judgment outcome in step 405 is [1, 1], it is found, using the connected region denoising method, that the pixel point is an isolated pixel point, then it is determined that the pixel point is not infarcted; therefore, the infarct judgment outcome in step S405 is corrected to [1, 0].

Step S409: further judging the infarct judgment outcomes regarding all target areas in the left and right cerebral hemispheres.

The infarct judgment outcomes regarding the 20 target areas outputted in step S407 possibly have a scenario that an early ischemia change is present in bilateral target areas. In normal circumstances, there should be only one side infarcted; if the early ischemia change is present at both sides, it needs to further determine which specific side is infarcted. The judgment may be made based on the principle that the side with the smaller greyscale change has a higher probability of infarct. For bilateral target areas in the left and right cerebral hemispheres, the smaller the ratio between bilateral greyscales, or the smaller the difference between bilateral greyscales, or the smaller the numerical value resulting from the combination of the ratio and the difference, the higher the confidence is; therefore, by comparing the minimum values among the ratios between bilateral greyscales, or the minimum differences between bilateral greyscales, or the minimum numerical values resulting from the combinations of the ratios and the differences in the target areas, the side with the smaller value, i.e., the side with a higher confidence, is determined to be infarcted, while the contralateral hemisphere is determined as not infarcted; the above outputted infarct judgment outcomes are then corrected based on the infarct judgment outcomes outputted in step S407.

Based on the algorithm described in step S407, the embodiment shown in FIG. 6 is subjected to infarct judgment using the ratio algorithm or the difference algorithm; then, the outputted infarct judgment outcomes for target areas 1~20 are provided below: 1: [0, 0.99, −0.5], 2: [1, 0.92, −2.7], 3: [1, 0.93, −2.4], 4: [0, 1, 0], 5: [0, 1.01, 0.2], 6: [0, 1.03, 0.9], 7: [0, 0.99, −0.5], 8: [0, 1.02, 0.5], 9: [0, 1.09, 2.7], 10: [0, 1.08, 2.4], 11: [0, 1, 0], 12: [0, 0.99, −0.2], 13:

[0, 0.97, −0.9], 14: [0, 1.01, 0.5], 15: [0, 1.05, 1.6], 16: [0, 1, 0], 17: [0, 1, 0], 18: [1, 0.95, −1.6], 19: [0, 1, 0], 20: [0, 1, 0].

In an embodiment of the present disclosure, the above outputted infarct judgment outcomes are subjected to further judgment based on the ratio-based confidence algorithm, wherein the minimum ratio in the left target areas is 0.92, and the minimum ratio in the right target areas is 0.95. Following the principle that the side with the smaller ratio has a higher confidence and is infarcted, the left side is infarcted. Further, the outputted infarct judgment outcome is corrected as such: correcting 18: [1, 0.95, −1.6] to 18: [0, 0.95, −1.6]; while the remained infarct judgment outcomes do not change; then the corrected infarct judgment outcomes regarding all target areas in the left and right cerebral hemispheres serve as updated infarct judgment outcomes for subsequent grading.

In an embodiment of the present disclosure, the above outputted infarct judgment outcomes are subjected to further judgment based on the difference-based confidence algorithm, wherein the minimum difference in the left target areas is −2.7, and the minimum difference in the right target areas is −1.6. following the principle that the side with the smaller difference has a higher confidence and is thus infarcted, due to −2.7<−1.6, the left side is infarcted. Further, the outputted infarct judgment outcome is corrected as such: correcting 18: [1, 0.95, −1.6] to 18: [0, 0.95, −1.6], while the remained infarct judgment outcomes do not change; then, the corrected infarct judgment outcomes serve as updated infarct judgment outcomes for subsequent grading.

In an embodiment of the present disclosure, the outputted infarct judgment outcomes are subjected to further judgment based on the confidence algorithm combining the ratio algorithm and the difference algorithm. This approach uses the function c=(ratio−0.5)/0.7+(diff+20)/50 to compute the c values of the outputted infarct judgment outcomes. The lower the c value, the higher the probability of infarct onset, i.e., the higher the confidence; by comparing the smallest c values of bilateral target areas, the side with the lower smallest c value is infarcted. The c values of the target areas are computed based on the infarct judgment outcomes outputted in the embodiment of FIG. 6 using the ratio algorithm or the difference algorithm; then the c values of the target areas 1~20 are consecutively: 1.09, 0.95, 0.97, 1.11, 1.13, 1.17, 1.09, 1.15, 1.30, 1.28, 1.11, 1.10, 1.05, 1.14, 1.22, 1.11, 1.11, 1.01, 1.11, 1.11; based on the outcomes of the c values, it is seen that the smallest c value at the left side is 0.95, while the smallest c value at the right side is 1.01; because 0.95<1.01, the left side is infarcted. Further, the outputted infarct judgment outcome is corrected as such: correcting 18: [1, 0.95, −1.6] to 18: [0, 0.95, −1.6], while the remained infarct judgment outcomes do not change; then, the corrected infarct judgment outcomes serve as updated infarct judgment outcomes for subsequent grading.

If the infarct judgment outcomes outputted by step S407 show that one side is infarcted, then it is unnecessary to perform further judgment, and the infarct judgment outcomes may be directly used in subsequent grading.

Step S411: outputting a grading outcome based on infarct judgment outcomes regarding all target areas in the left and right cerebral hemispheres.

Based on the infarct judgment outcomes regarding all target areas in the left and right cerebral hemispheres outputted in step S409, wherein the weight of each target area is 1 point and the total points is 10 points, by subtracting the number of infarcted target areas from the 10 points, the resulting value is the grading outcome. Specifically, the target areas 1~20 are traversed to screen, from the outputted infarct judgment outcomes, arrays whose first element is 1, and the number as counted is the number of infarcted target areas. In grading, 1 point is deducted for each infarcted target area; the finally obtained number is the grading outcome.

In an embodiment of the present disclosure, an outputted grading outcome may be an ASPECTS value, which is a result obtained based on performing infarct judgments twice on the target areas in the left and right cerebral hemispheres. The outputted grading outcome may also be two ASPECTS values, respectively representing the ASPECTS values of the left and right cerebral hemispheres. If the grading outcome is represented by two ASPECTS values, in a specific application, the grading outcome for the corresponding side may be directly outputted based on the infarcted side determined with a known symptom, without a need of performing infarct judgments twice on the target areas in the left and right cerebral hemispheres. If the known symptom exhibits left hemiplegia, it is seen that the right cerebral hemisphere is infarcted; then during grading, the grading outcome regarding the right cerebral hemisphere may be directly outputted.

The cranial CT-based grading method for anterior circulation may also be applied to posterior circulation. In the specific implementation process, the cranial CT-based grading method for posterior circulation has somewhat differences from that for the anterior circulation. For example, the target areas for posterior circulation are: pons, bilateral cerebella, midbrain, bilateral thalami, and bilateral PCA-territories, and the digital labels are: 0 representing background, 1 representing pons, 2 representing left cerebellum, 3 representing right cerebellum, 4 representing midbrain, 5 representing left thalamus, 6 representing right thalamus, 7 representing left PCA-territory, and 8 representing right PCA-territory. The features as extracted during extracting target areas are also different from those for the anterior circulation. Because in posterior-circulation target areas, not all areas are present in both left and right cerebral hemispheres, e.g., the pons and the midbrain need not be subjected to bilateral infarct judgment, the infarct judgment is also performed differently from that for the anterior circulation. Besides, in posterior circulation grading, the weights of respective target areas also differ from the anterior circulation. Specifically, for posterior-circulation ASPECTS assessment, the weights of the pons and the midbrain are 2, while the weights of remained areas are all 1.

Irrespective of anterior circulation grading or posterior circulation grading, all ideas based on the written description of the present disclosure or all improved methods proposed based on the present disclosure fall within the protection scope of the present disclosure.

What have been elaborated above is a cranial CT-based grading method; correspondingly, the present disclosure further provides a cranial CT-based grading system, as shown in FIG. 7, which specifically comprises:

an area extracting module configured for extracting target areas from to-be-processed multi-frame cranial CT data, wherein the target areas refer to areas for being graded in the cranial CT data;

an infarct identifying module configured for performing infarct judgment on each target area included in the target areas to output an infarct judgment outcome regarding the target area; and a grading module configured for outputting a grading outcome based on infarct judgment outcomes regarding all target areas.

What have been described above are preferred embodiments of the present disclosure. The other embodiments fall within the scope of the appended claims. In some cases, the actions or steps disclosed in the claims may be executed according to a sequence different from those disclosed in the embodiments but may still achieve a desired result. Additionally, it is not compulsory for to follow the specific sequence or continuous sequence as illustrated in the drawings to achieve the desired result. In some embodiments, multi-task processing or concurrent processing is optional or likely beneficial.

Respective embodiments in the specification are described in a progressive manner, and same or similar parts between various embodiments may be referenced to each other, while each embodiment focuses on differences from other embodiments. Particularly, for an apparatus embodiment, an electronic device embodiment, and a non-volatile computer storage medium embodiment, because they are basically similar to the method embodiments, they are not detailed here and may refer to the depictions in the corresponding method embodiments.

The apparatus, electronic device, and non-volatile computer storage medium provided in the embodiments of the present disclosure correspond to the method; therefore, the apparatus, electronic device, and non-volatile computer storage medium also have beneficial effects of the corresponding method. As the beneficial effects of the method have been illustrated in detail, they will not be detailed here.

In 1990s, improvement of a technology may be apparently differentiated into hardware improvement (e.g., improvement of a circuit structure of a diode, a transistor, a switch, etc.) or software improvement (e.g., improvement of a method process). However, with development of technology, currently improvement of many method processes may be regarded as direct improvement to a hardware circuit structure. Designers always program an improved method process into a hardware circuit to obtain a corresponding hardware circuit structure. Therefore, it is improper to allege that improvement of a method process cannot be implemented by a hardware entity module. For example, a programmable logic device (PLD) (such as a field programmable gate array FPGA) is such an integrated circuit, a logic function of which is determined by programming a corresponding device. A designer may integrate a digital system on a piece of PLD by programming, without a need of engaging a chip manufacturer to design and fabricate a dedicated integrated circuit chip. Moreover, currently, in replacement of manual fabrication of an integrated circuit chip, this programming is mostly implemented by a logic compiler, which is similar to a software compiler used when developing and writing a program. To compile the previous original code, a specific programming language is needed, which is referred to as a hardware description language (HDL). Further, there are more than one HDLs, e.g., ABEL (Advanced Boolean Expression Language), AHDL (Altera Hardware Description Language), Confluence, CUPL (Cornell University Programming Language), HDCal, JHDL (Java Hardware Description Language), Lava, Lola, MyHDL, PALASM, RHDL (Ruby Hardware Description Language), among which, VHDL (Very-High-Speed Integrated Circuit Hardware Description Language) and Verilog are used most prevalently. Those skilled in the art should also understand that a hardware circuit for a logic method process can be easily implemented by subjecting, without much efforts, the method process to logic programming using the above hardware descriptive languages into an integrated circuit.

A controller may be implemented according to any appropriate manner. For example, the controller may adopt manners such as a microprocessor or processor and a computer readable medium storing computer readable program codes (e.g., software or firmware) executable by the (micro) processor, a logic gate, a switch, an application specific integrated circuit (ASIC), a programmable logic controller, and an inlaid microcontroller. Examples of the controller include, but are not limited to, the following microcontrollers: ARC 625D, Atmel AT91SAM, Microchip PIC18F26K20 and Silicone Labs C8051F320. The memory controller may also be implemented as part of the control logic of the memory. Those skilled in the art may further understand that besides implementing the controller by pure computer readable program codes, the method steps may be surely subjected to logic programming to enable the controller to implement the same functions in forms of a logic gate, a switch, an ASIC, a programmable logic controller, and an inlaid microcontroller, etc. Therefore, the controller may be regarded as a hardware component, while the modules for implementing various functions included therein may also be regarded as the structures inside the hardware component. Or, the modules for implementing various functions may be regarded as software modules for implementing the method or structures inside the hardware component.

The system, apparatus, module or unit illustrated by the embodiments above may be implemented by a computer chip or entity, or implemented by a product having a certain function. A typical implementation device is a computer. Specifically, the computer for example may be a personal computer, a laptop computer, a cellular phone, a camera phone, a smart phone, a personal digital assistant, a media player, a navigation device, an email device, a game console, a tablet computer, a wearable device, or a combination of any of these devices.

To facilitate description, the apparatuses above are partitioned into various units by functions to describe. Of course, when implementing one or more embodiments of the present application, functions of various units may be implemented in one or more pieces of software and/or hardware.

Those skilled in the art should understand that the embodiments of the present disclosure may be provided as a method, a system, or a computer program product. Therefore, the embodiments of the present disclosure may adopt a form of complete hardware embodiment, a complete software embodiment, or an embodiment combining software and hardware. Moreover, the embodiments of the present disclosure may adopt a form of a computer program product implemented on one or more computer-adaptable storage media including computer-adaptable program code (including, but not limited to, a magnetic disc memory, CD-ROM, and optical memory, etc.).

The present disclosure is described with reference to the flow diagram and/or block diagram of the method, apparatus (system) and computer program product according to the embodiments of the present disclosure. It needs to be noted that each flow and/or block in the flow diagram and/or block diagram, and a combination of the flow and/or block in the flow diagram and/or block diagram, may be implemented by computer program instructions. These computer program instructions may be provided to a processor of a general-purpose computer, a dedicated computer, an embedded processor, or other programmable data processing device to generate a machine, such that an apparatus for implementing the functions specified in one or more flows of the flow diagram and/or one or more blocks in the block diagram is implemented via the computer or the processor of other programmable data processing device.

These computer program instructions may also be stored in a computer readable memory that may boot the computer or other programmable data processing device to work in a specific manner such that the instructions stored in the computer readable memory to produce a product including an instruction apparatus, the instruction apparatus implementing the functions specified in one or more flows of the flow diagram and/or in one or more blocks in the block diagram.

These computer program instructions may be loaded on the computer or other programmable data processing device, such that a series of operation steps are executed on the computer or other programmable device to generate a processing implemented by the computer, such that the instructions executed on the computer or other programmable device provide steps for implementing the functions specified in one or more flows of the flow diagram and/or one or more blocks in the block diagram is implemented via the computer or the processor of other programmable data processing device.

In a typical configuration, the computing device includes one or more processors (CPUs), an input/output interface, a network interface, and a memory.

The memory may include a non-permanent memory in a computer readable medium, a random-access memory (RAM) and/or a non-volatile memory, e.g., a read-only memory (ROM) or a flash memory (flash RAM). The memory is an example of a computer readable medium.

The computer readable memory includes a permanent type, non-permanent type, a mobile type, and a non-mobile type, which may implement information storage by any method or technology. The information may be a computer-readable instruction, a data structure, a module of a program or other data. Examples of the memory mediums of the computer include, but are not limited to, a phase-change RAM (PRAM), a static random access memory (SRAM), a dynamic random access memory (DRAM), other type of random access memory (RAM), a read-only memory (ROM), an electrically erasable programmable read only memory (EEPROM), a flash memory body or other memory technology, a CD-ROM (Compact Disc Read-Only Memory), a digital multi-function optical disc (DVD) or other optical memory, a magnetic cassette type magnetic tape, a magnetic tape disc memory, or other magnetic storage device or any other non-transmission medium which may be configured for storing information to be accessed by a computing device. Based on the definitions in the specification, the computer readable medium does not include a transitory media, e.g., a modulated data signal and a carrier.

It needs also be noted that the terms "include," "comprise" or any other variables intend for a non-exclusive inclusion, such that a process, a method, a product or a system including a series of elements not only includes those elements, but also includes other elements that are not explicitly specified or further includes the elements inherent in the process, method, product or system. Without more restrictions, an element limited by the phase "including one . . . " does not exclude a presence of further equivalent elements in the process, method, product or system including the elements.

The present application may be described in a general context of the computer-executable instruction executed by the computer, for example, a program module. Generally, the program module includes a routine, a program, an object, a component, and a data structure, etc., which executes a specific task or implements a specific abstract data type. The present application may be practiced in a distributed computing environment, in which a task is performed by a remote processing device connected via a communication network. In the distributed computing environment, the program module may be located on a local or remote computer storage medium, including the memory device.

Respective embodiments in the specification are described in a progressive manner, and same or similar parts between various embodiments may be referenced to each other, while each embodiment focuses on differences from other embodiments. Particularly, for a system embodiment, because it is substantially similar to the method embodiment, it is described relatively simply. Relevant parts may refer to the method embodiments.

What have been described above are only preferred embodiments of the present disclosure, not for limiting the present disclosure; to those skilled in the art, the present disclosure may have various alterations and changes. Any modifications, equivalent substitutions, and improvements within the spirit and principle of the present disclosure should be included within the protection scope of the present disclosure.

We claim:

1. A cranial CT-based grading method, comprising:
   extracting, by a processor, target areas in the left and right cerebral hemispheres from to-be-processed multi-frame cranial CT data, wherein the target areas refer to areas for being graded in the cranial CT data;
   performing, by the processor, infarct judgment on each target area included in the target areas to output an infarct judgment outcome regarding the target area; and
   outputting, by the processor, a grading outcome based on infarct judgment outcomes regarding all target areas;
   wherein performing the infarct judgment on each target areas comprises:
   classifying, by the processor, each pixel point in the to-be-processed multi-frame CT using digital labels, the digital labels being in one-to-one correspondence with the target areas in the left and right cerebral hemispheres;
   judging, by the processor, a specific area to which the pixel point belongs in the target areas in the left and right cerebral hemispheres;
   locating, by the processor, same target areas in the left and right cerebral hemispheres in the to-be-processed multi-frame CT based on the digital label;
   traversing, by the processor, all pixel points on each target area;
   summing and averaging, by the processor, the greyscale values of all pixel points in the target area meeting the greyscale value condition, wherein the average value serves as the average greyscale value of the target area;
   comparing, by the processor, the average greyscale value of the target area with the average greyscale value of the contralateral target area, to judge whether the target area is infarcted.

2. The method according to claim 1, wherein the extracting target areas from to-be-processed multi-frame cranial CT data specifically comprises:
   inputting the to-be-processed cranial CT data into a model, and classifying each pixel point in the cranial CT data using digital labels to output a three-dimensional matrix with digital labels, the three-dimensional matrix being in correspondence with respective pixel points in the cranial CT data, wherein the digital labels are in one-to-one correspondence with the target areas.

3. The method according to claim 1, wherein the performing infarct judgment on each target area included in the target areas to output an infarct judgment outcome regarding the target area specifically comprises:
    performing infarct judgment on each pixel point included in the target area to output an infarct judgment outcome regarding the target area.

4. The method according to claim 1, wherein the performing infarct judgment on each target area included in the target areas to output an infarct judgment outcome regarding the target area further comprises:
    judging, based on the infarct judgment outcome regarding the target area, whether infarct is indicated in the target area in both left and right cerebral hemispheres; and
    if infarct is indicated in the target area in both left and right cerebral hemispheres, further determining which specific side is infarcted, and correcting the infarct judgment outcome regarding the target area as an updated infarct judgment outcome regarding the target area.

5. The method according to claim 1, wherein the outputting a grading outcome based on infarct judgment outcomes regarding all target areas specifically comprises:
    determining all infarcted target areas based on the infarct judgment outcomes regarding all target areas; and;
    subtracting, based on weights allotted to respective target areas, weights of the infarcted target areas from the total score to output a resulting value as the grading outcome.

6. A cranial CT-based grading system, comprising:
    one or more processors configured to execute a method comprising:
    extracting target areas in the left and right cerebral hemispheres from to-be-processed multi-frame cranial CT data, wherein the target areas refer to areas for being graded in the cranial CT data;
    performing infarct judgment on each target area included in the target areas to output an infarct judgment outcome regarding the target area; and
    outputting a grading outcome based on infarct judgment outcomes regarding all target areas;
    wherein performing the infarct judgment on each target areas comprises:
    classifying each pixel point in the to-be-processed multi-frame CT using digital labels, the digital labels being in one-to-one correspondence with the target areas in the left and right cerebral hemispheres;
    judging a specific area to which the pixel point belongs in the target areas in the left and right cerebral hemispheres;
    locating same target areas in the left and right cerebral hemispheres in the to-be-processed multi-frame CT based on the digital label;
    traversing all pixel points on each target area;
    summing and averaging the greyscale values of all pixel points in the target area meeting the greyscale value condition, wherein the average value serves as the average greyscale value of the target area;
    comparing the average greyscale value of the target area with the average greyscale value of the contralateral target area, to judge whether the target area is infarcted.

7. The system according to claim 6, wherein the extracting target areas from to-be-processed multi-frame cranial CT data specifically comprises:
    inputting the to-be-processed multi-frame cranial CT data into a model, and classifying each pixel point in the cranial CT data using digital labels to output a three-dimensional matrix with digital labels, the three-dimensional matrix being in correspondence with respective pixel points in the cranial CT data, wherein the digital labels are in one-to-one correspondence with the target areas.

8. The system according to claim 6, wherein the performing infarct judgment on each target area included in the target areas to output an infarct judgment outcome regarding the target area specifically comprises:
    performing infarct judgment on each pixel point included in the target area to output an infarct judgment outcome regarding the target area.

9. The system according to claim 6, wherein the performing infarct judgment on each target area included in the target areas to output an infarct judgment outcome regarding the target area further comprises:
    judging, based on the infarct judgment outcome regarding the target area, whether infarct is indicated in the target area in both left and right cerebral hemispheres; and
    if infarct is indicated in the target area in both left and right cerebral hemispheres, further determining which specific side is infarcted, and correcting the infarct judgment outcome regarding the target area as an updated infarct judgment outcome regarding the target area.

10. The system according to claim 6, wherein the outputting a grading outcome based on infarct judgment outcomes regarding all target areas specifically comprises:
    determining all infarcted target areas based on the infarct judgment outcomes regarding all target areas; and;
    subtracting, based on weights allotted to respective target areas, weights of the infarcted target areas from the total score to output a resulting value as the grading outcome.

* * * * *